United States Patent
Al-Jazaeri (10) Patent No.: US 9,895,146 B1
(45) Date of Patent: Feb. 20, 2018

(54) WOUND CLOSURE DEVICE

(71) Applicant: KING SAUD UNIVERSITY, Riyadh (SA)

(72) Inventor: Ayman Al-Jazaeri, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/714,986

(22) Filed: Sep. 25, 2017

(51) Int. Cl.
*A61B 17/04* (2006.01)
*A61B 17/12* (2006.01)
*A61B 17/06* (2006.01)
*A61B 17/00* (2006.01)

(52) U.S. Cl.
CPC .... *A61B 17/0469* (2013.01); *A61B 17/06166* (2013.01); *A61B 2017/00004* (2013.01); *A61B 2017/00367* (2013.01); *A61B 2017/00623* (2013.01); *A61B 2017/00663* (2013.01); *A61B 2017/047* (2013.01); *A61B 2017/0409* (2013.01); *A61B 2017/0412* (2013.01); *A61B 2017/0472* (2013.01); *A61B 2017/061* (2013.01)

(58) Field of Classification Search
None
See application file for complete search history.

(56) References Cited

U.S. PATENT DOCUMENTS

| | | | |
|---|---|---|---|
| 5,527,321 A * | 6/1996 | Hinchliffe | A61B 17/0469 112/169 |
| 8,834,493 B2 | 9/2014 | Boehlke et al. | |
| 9,301,760 B2 | 4/2016 | Fox | |
| 9,314,229 B2 * | 4/2016 | Argentine | A61B 17/0057 |
| 9,326,764 B2 * | 5/2016 | Nobles | A61B 17/0469 |
| 9,414,820 B2 | 8/2016 | Voss et al. | |
| 9,504,464 B2 | 11/2016 | Campbell et al. | |
| 9,549,728 B2 | 1/2017 | Chu | |
| 9,572,570 B2 | 2/2017 | Gellman et al. | |
| 9,681,868 B2 * | 6/2017 | Prior | A61B 17/06166 |
| 2003/0028201 A1 * | 2/2003 | Navarro | A61B 17/0057 606/139 |
| 2003/0167063 A1 * | 9/2003 | Kerr | A61B 17/0057 606/144 |
| 2003/0171764 A1 * | 9/2003 | Debbas | A61B 17/0057 606/144 |
| 2005/0149066 A1 * | 7/2005 | Stafford | A61B 17/0057 606/144 |
| 2008/0033459 A1 * | 2/2008 | Shafi | A61B 17/0057 606/144 |
| 2010/0145364 A1 * | 6/2010 | Keren | A61B 17/0469 606/144 |
| 2010/0179572 A1 * | 7/2010 | Voss | A61B 17/0057 606/144 |
| 2011/0218568 A1 * | 9/2011 | Voss | A61B 17/04 606/232 |

(Continued)

*Primary Examiner* — Amy R Weisberg
(74) *Attorney, Agent, or Firm* — Richard C. Litman (57) ABSTRACT

The wound closure device includes an outer tubular housing, an inner shaft that extends through the housing, a needle control assembly at least partially disposed with the housing, a pair of hollow needles in communication with the needle control assembly, sutures in the housing, and a suture deployment assembly connected to a distal end of each suture and to the inner shaft. The needles can be inserted into a tissue to deposit the sutures and suture anchors at or near wound edges. The needles can thereafter be completely withdrawn from the tissue.

8 Claims, 7 Drawing Sheets

(56) References Cited

U.S. PATENT DOCUMENTS

| | | | |
|---|---|---|---|
| 2011/0270282 A1* | 11/2011 | Lemke | A61B 17/0057 606/148 |
| 2014/0148825 A1* | 5/2014 | Nobles | A61B 17/0469 606/145 |
| 2014/0350576 A1* | 11/2014 | Patel | A61B 17/0482 606/145 |
| 2015/0039025 A1* | 2/2015 | Prior | A61B 17/0482 606/228 |
| 2015/0216514 A1* | 8/2015 | Weisbrod | A61B 17/0401 606/232 |
| 2016/0228107 A1* | 8/2016 | Madsen | A61B 17/3417 |
| 2016/0242764 A1 | 8/2016 | Garrison et al. | |
| 2016/0345965 A1 | 12/2016 | Ho et al. | |
| 2016/0367234 A1 | 12/2016 | Fortson et al. | |
| 2017/0049426 A1 | 2/2017 | Gianotti et al. | |
| 2017/0105712 A1* | 4/2017 | Patel | A61B 17/0057 |
| 2017/0189061 A1* | 7/2017 | Weisbrod | A61B 17/3423 |

\* cited by examiner

WOUND CLOSURE DEVICE

BACKGROUND OF THE INVENTION

1. Field of the Invention

The present invention relates generally to medical devices, and particularly to a wound closure device.

2. Description of the Related Art

Typically, wounds, such as puncture wounds created by trocars during minimally invasive surgeries, have free edges. Other types of wounds can result from defects in the skin, muscles, bowels, bones, or other tissues. Leaving such wounds open can lead to further infection and additional complications. For example, leaving punctures wounds created by trocars open can lead to port site hernias, which are the incisional hernias that occur after minimally invasive surgery at the trocar incision site. The recent wide adoption of minimally invasive surgery including laparoscopic surgery for many diagnostic and therapeutic procedures has increased the occurrence of trocar site hernias by approximately 1% to 6%, along with their related complications, such as bowel or omentum incarceration, or intestinal occlusion or perforation. Accordingly, the post-site fascial defect has to be closed completely during the procedure.

Wounds are normally closed by using a stitch-in-needle technique to manually close the wound using needle holders and forceps. The procedure is not only cumbersome and time consuming, but may be quite difficult when closing a smaller puncture wound resulting from a minimally invasive procedure, particularly in obese patients. Moreover, sewing the fascia layer closed has an associated risk of stitching the underlying bowels which can lead to serious complications. Thus, the closure quality can vary since such closures depend heavily on the human operator's skills.

Various devices can be used for wound closure which take the form of a simple sharp suture passer, or devices having an upward or downward pointing needle(s) on a shaft that suture the fascia layer from inside out. However, with these devices, a medical practitioner cannot control the distance between the device shaft and the needle tip to control the width of the wound edges incorporated in the closure or even the depth of the device tip penetration. Accordingly, such devices are incapable of delivering a suture across the wound while simultaneously controlling the depth and width of the penetrated wound edges.

Thus, a wound closure device solving the aforementioned problems is desired.

SUMMARY OF THE INVENTION

The wound closure device includes an outer tubular housing, an inner shaft that extends through the housing, a needle control assembly 130 at least partially disposed with the housing, a pair of hollow needles in communication with the needle control assembly, a pair of suture portions in the housing, and a suture deployment assembly connected to a distal end of the suture portions and to the inner shaft. The needles can be inserted into a tissue to deposit the sutures and suture anchors at or near wound edges, and completely withdrawn after tissue insertion.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

FIGS. 1 through 12 show a wound closure device 100 configured for closing a wound W. The wound closure device 100 can be used to close small wounds, e.g, a fascia wound caused by a laparoscopic cannula insertion, a thoracoscopic wound, an incisional fascia wound, or any skin wound or to approximate any tissue edges.

The wound closure device 100 includes an outer tubular housing 110, an inner shaft 115 that extends through the housing 110, a needle control assembly 130 at least partially disposed with the housing 110, a pair of hollow needles 125 in communication with the needle control assembly 130, a suture 147 in opposing sides of the housing 110 (e.g., grooves defined in housing wall), and a suture deployment assembly 160 connected to a distal end of each suture 147 and to the inner shaft 115. Although two hollow needles 125 are shown in the embodiments depicted in the figures, other embodiments can include any number of hollow needles 125, e.g., one or more, and an equal number of corresponding structural components, e.g., suture pusher, suture anchor, suture deploying rods, for deploying the needles into a tissue.

The housing 110 includes a proximal portion 112a including a proximal end 114a, and a distal portion 112b including a distal end 114b. Side openings 500a, 500b extend through a wall of the tubular housing 110 at a proximal portion 112a thereof. The proximal portion 112a of the tubular housing 110 further includes an outer surface having a threaded portion 117a. The distal portion 112b of the tubular housing 110 includes a pair of needle hatches 185.

Figure 5A:
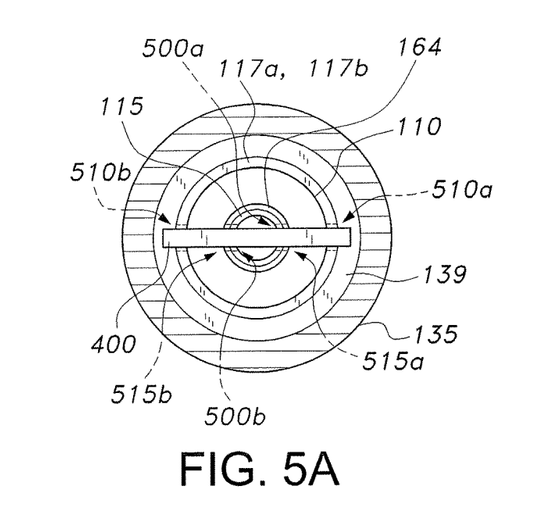
FIG. 5A is a top, cross sectional view of the wound closure device, according to the present invention.

The inner shaft 115 extends vertically through the tubular housing 110 and includes one end connected, such as fused, with the proximal end 114a and an opposing end connected, such as fused, with the distal end 114b of the tubular housing 110, respectively. The inner shaft 115 includes two opposing longitudinal side openings 510a and 510b (FIG. 5A), aligned with the corresponding side opening 500a, 500b of the tubular housing 110, as illustrated in FIG. 5A.

Figure 1:
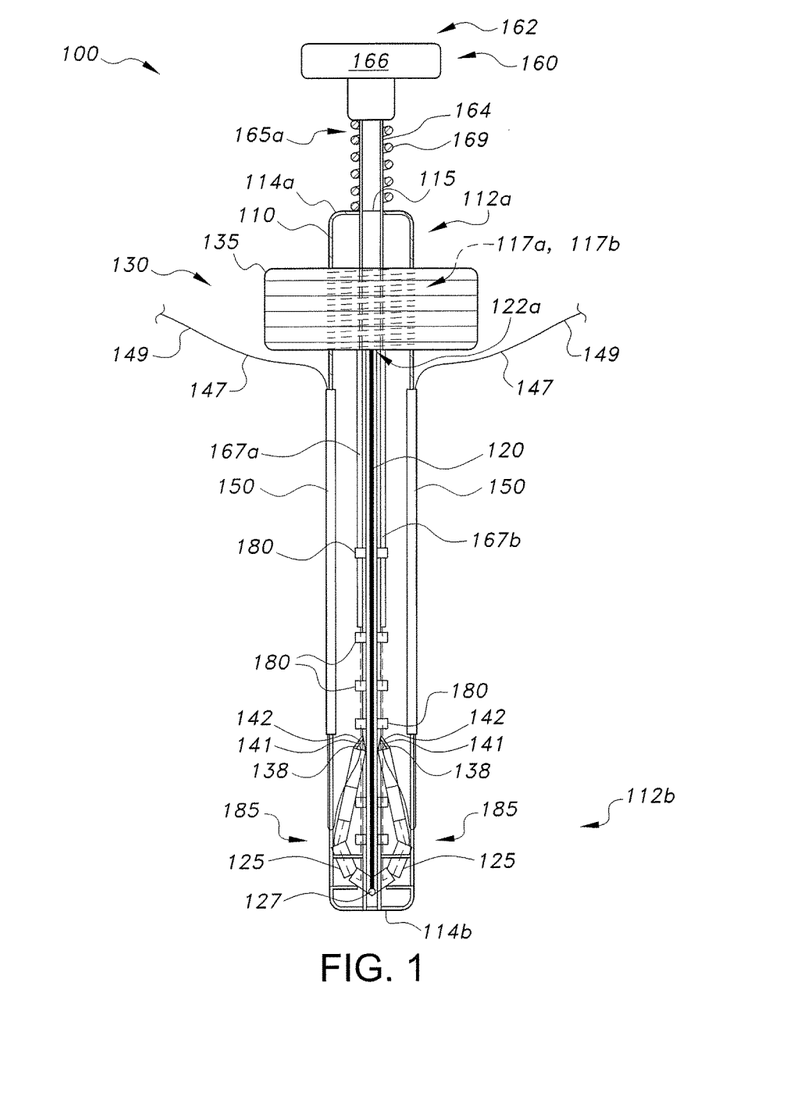
FIG. 1 is an environmental view of a wound closure device having a pair of hollow needles, according to the present invention.
Figure 2:
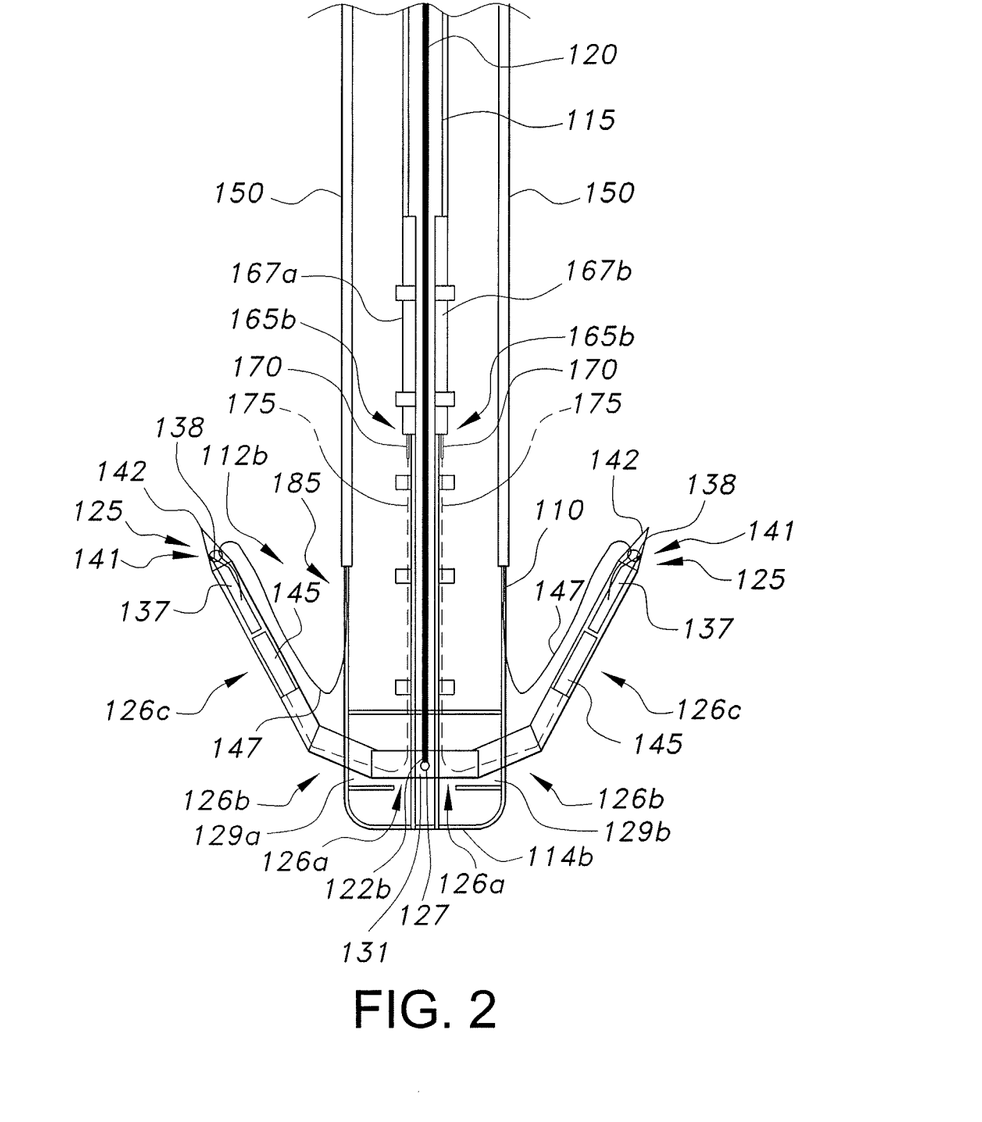
FIG. 2 illustrates each hollow needle being deflected through a corresponding hatch positioned on the lower portion of the wound closure device, according to the present invention.

The suture deployment assembly 160 includes a depressible plunger 162 having a suture deploying shaft 164. A knob 166 is attached to a proximal end 165a of the shaft 164 and a pair of suture deploying rods 170 is attached to a distal end 165b of the shaft 164. Each suture deploying rod 170 is attached to a first end of a respective suture deploying wire 175. A second, opposing end of each suture deploying wire 175 is attached to a respective anchor pusher 145. As will be described in detail below, each anchor pusher 145 is at least partially disposed within a respective hollow needle 125, adjacent a suture anchor 137, the suture anchor 137 having a tip 138, such as a sharp tip or a blunt tip. A plurality of longitudinal channels, such as a first longitudinal channel 167a and a second longitudinal channel 167b, can extend vertically along the suture deploying shaft 164. Each suture deploying rod 170 may run through the corresponding longitudinal channel 167a, 167b of the suture deployment shaft 164. A compressible member 169, such as a spring, may be positioned around a portion of the shaft 164, between the knob 166 and the proximal end 114a of the tubular housing 110, as illustrated in FIG. 1. Alternatively, the compressible member 169 can be positioned with the shaft 164.

The suture deploying shaft 164 can have a diameter greater than a diameter of the inner shaft 115. The suture deploying shaft 164 can slide vertically along the outer surface of the inner shaft 115. The proximal portion of the suture deploying shaft 164 also includes two opposing longitudinal side openings 515a and 515b (FIG. 5A). Each of the side opening 515a, 515b are aligned with each of the corresponding side opening 500a, 500b of the tubular housing 110 and with each corresponding side opening 510a, 510b of the inner shaft 115, forming a track 139. Each suture deploying rod 170 and corresponding suture deploying wire 175 runs parallel to the inner shaft 115. Each suture deploying wire 175 can be stiff, e.g, braided, to resist excessive undesired bending when pushed downward by the corresponding suture deploying rod 170. Each suture deploying rod 170 and corresponding suture deploying wire 175 can be loosely secured to the exterior of the inner shaft 115 by a stabilizer ring 180 positioned along the outer wall surface of the inner shaft 115.

The needle control assembly includes a needle control rod 120 positioned within the inner shaft 115, a hinge mechanism 127 in communication with a distal end 122b of the needle control rod 120, and two needle stabilizer sheets 129a, 129b for supporting the hollow needles 125. A central opening 131 extends between the stabilizer sheets 129a and 129b. A needle control bar 400 is connected to a proximal end 122a of the needle control rod 120. A needle control handle 135 is attached to the needle control bar 400 (FIG. 4) and includes a threaded inner portion 117b configured for threadedly engaging the outer threaded portion 117a of the tubular housing 110. The needle control bar 400 extends through the handle 135 and through the track 139, formed by the aligned openings 515a and 515b of the suture deploying shaft 164, openings 500a, 500b of the tubular housing 110, and openings 510a, 510b of the inner shaft. The needle control bar 400 may include a connecting member 410 positioned at the center of the needle control bar 400 for engaging the proximal end 122a of the needle control rod 120. As described below, manipulation of the handle 135, initiates movement of each hollow needle 125.

Figure 3A:
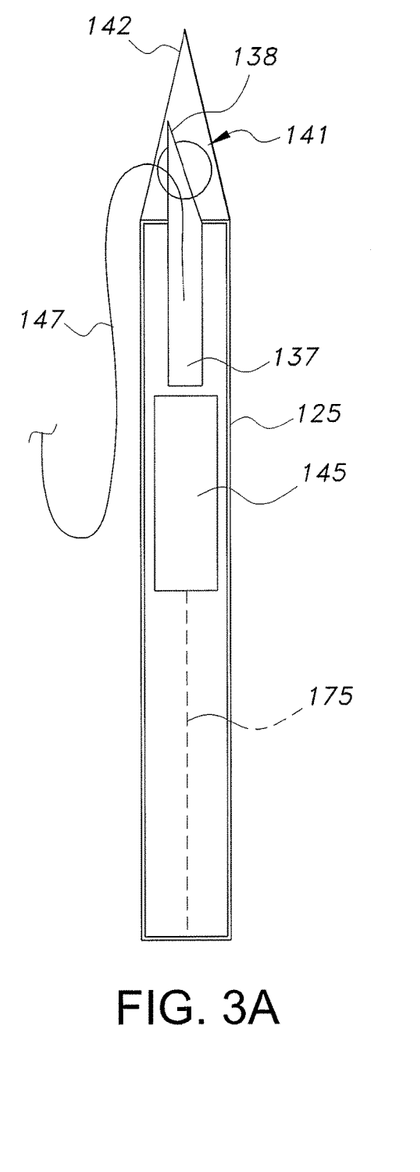
FIG. 3A illustrates an elongated distal portion of the hollow needle having a tip including an opening through which a suture anchor may be deployed, according to the present invention.
Figure 3B:
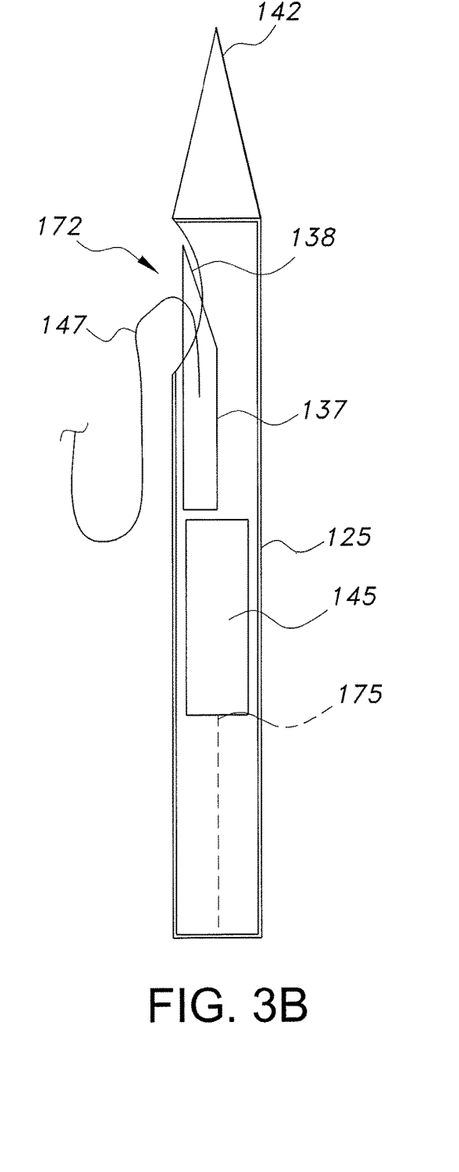
FIG. 3B illustrates an elongated distal portion of the hollow needle including an opening positioned on the side of the hollow needle facing towards the wound closure device through which a suture anchor may be ejected, according to the present invention.

Each hollow needle 125 houses the suture anchor 137 which is attached to one end of the suture 147. Each hollow needle 125 can include a sharp tip 142, such as a beveled sharp tip, so as to permit wound penetration. Each tip 142 can have an opening 141 through which the suture anchor 137 may be deployed. Preferably, the tip 142 is a beveled, sharp tip, and tip 138 of the suture anchor 137 is blunt to prevent or substantially prevent injury from the suture anchor 137 after deployment and/or disengagement of the suture anchor 137 when the hollow needle 125 is pulled back. It is to be noted that, as illustrated in FIG. 3B, each hollow needle 125 may include an alternative opening 172 positioned on the side, such as on the side facing towards the housing 110 of the wound closure device 100, through which the suture anchor 137 may be deployed.

Each anchor pusher 145 is at least partially disposed within a respective one of the hollow needles 125, adjacent a respective suture anchor 137. Each needle 125 is pivotally connected to the hinge mechanism 127. Vertical movement of the hinge mechanism 127 pivots the needles 125 outwardly or inwardly, as described in detail below. Each hollow needle 125 may have a straight proximal portion 126a and an elongated distal portion 126c to provide a "V" configuration once each hollow needle 125 is extended into the wound W. Alternatively, a curved middle portion 126b may extend between the straight distal portion 126c and the straight proximal portion 126a. The straight proximal portion 126a can include a grooved portion in which the suture deploying wire 175 may slide through as the suture deploying wire 175 enters the hollow needle 125.

Figure 4:
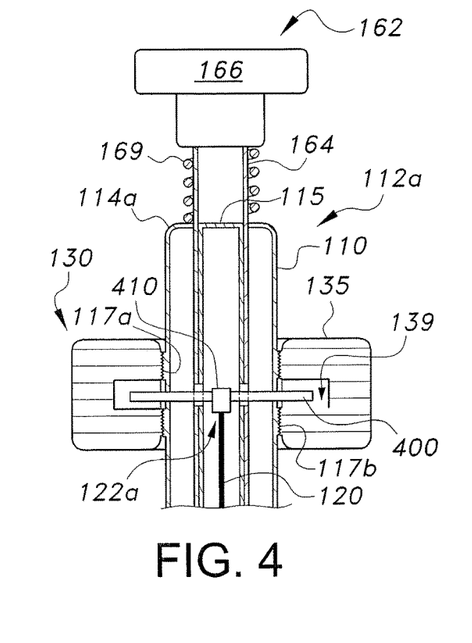
FIG. 4 is a partial, cross sectional view of the upper portion of the wound closure device, according to the present invention.
Figure 5B:
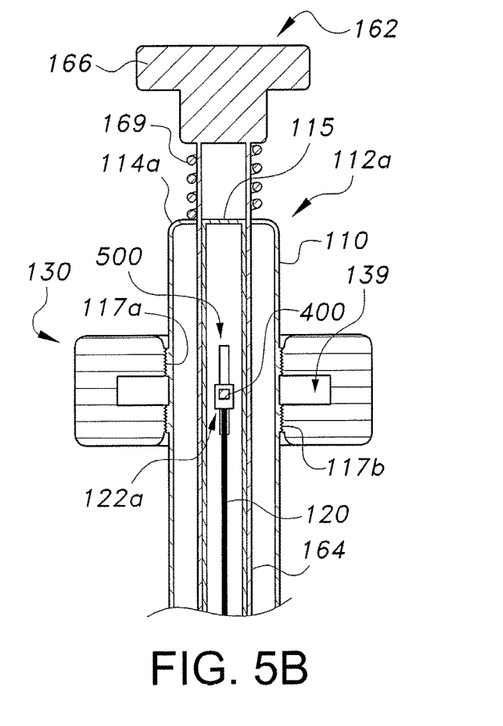
FIG. 5B is a partial, cross sectional side view of the upper portion of the wound closure device, according to the present invention.
Figure 5C:
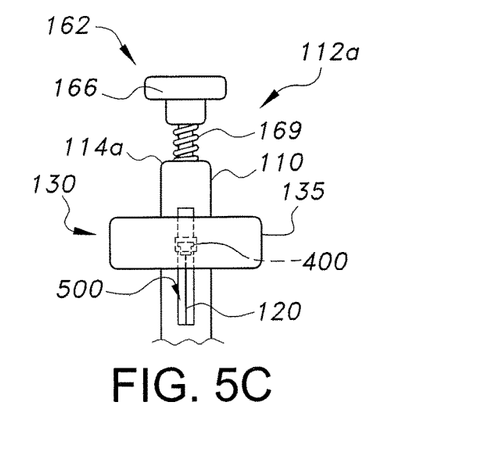
FIG. 5C is a partial, side view of the upper portion of the wound closure device, according to the present invention.

The needle control bar 400 extends horizontally through each of the opposing longitudinal side windows 500a and 500b, 510a and 510b, as well as 515a and 515b of the tubular housing 110, the suture deploying shaft 164, and the inner shaft 115, respectively, of the device 100, as illustrated in FIGS. 4, 5B, and 5C. As illustrated in FIG. 5A, the inner shaft 115 has a diameter less than the suture deploying shaft 164.

The tubular housing 110 can be an elongated hollow tube, made of any suitable type of medical grade material, such as plastic, and can have any suitable length. The stiffness, flexibility, and length of the tubular housing 110 and its contents can vary depending on the location of the wound W needing to be closed.

The needle control handle 135 can be configured for positioning on the threaded portion 177 of the tubular housing 110. Rotation of the needle control handle 135 can move the needle control handle 135 vertically along the tubular housing 110, e.g., upward or downward depending upon the direction of rotation. The vertical movement of the needle control handle 135, in turn, moves the needle control bar 400 vertically, such as in an upward direction and downward direction, within the track 139. Vertical movement of the needle control bar 400, such as in an upward direction or downward direction moves the needle control rod 120 accordingly. In operation, upward movement of the needle control bar 400 causes the needle control rod 120 to move upwardly and thereby triggers the attached hinge mechanism 127 to move upward through the central opening 131 and pivot the hollow needles 125 away from the device, through needle hatches 185. Once extended, the hollow needles 125 may form a "V" configuration or a "U" configuration, as illustrated in FIGS. 7-10. Similarly, downward movement of the needle control bar 400 causes the needle control rod 120 to move downwardly and thereby triggers the attached hinge mechanism to move downward through the central opening 131 and pivot the hollow needles 125 toward the housing. The side openings 500a and 500b, 510a and 510b, and 515a and 515b can have any suitable length and width sufficient to allow for upward and downward movement of the needle control bar 400 when the needle control handle 135 is rotated. The amount of movement of the needle control bar can determine the degree or angle at which the needles extend away from the housing 110 or the distance between each needle tip and the housing 110. Since wound sizes can vary significantly, controlling the distance between the tubular housing 110 and each hollow needle 125 may allow a medical professional to select a variable wound edge width for the closure procedure.

The suture anchor 137 can have any suitable shape, such as a rod or plate configuration, and can be formed from any suitable medical grade biodegradable material, such as polyglycolides, polylacides, polydioxanone, copolymers, as well as any absorbably synthetic or naturally occurring material. Accordingly, since the suture anchor 137 can be biodegradable, the suture anchor 137 may not have to be retrieved once the suture anchor 137 has been deployed into the wound W, e.g., fascia layer FL.

The suture 147 can be attached at the center of the corresponding suture anchor 137 thereby dispersing the tissue pressure on its wider dimension once under tension during the closure of the wound W. The free end 149 (e.g. the end not attached to the suture anchor 137) of each suture 147 can extend outward from the channel 150 adjacent the proximal portion 112a of the tubular housing 110, such as beneath the needled control handle 135, as illustrated in FIG. 1. Alternatively, each channel 150 and corresponding suture 147 can be positioned alongside the interior surface of the tubular housing 110 extending from beneath the needle control handle 135 such that the free end 149 of each suture 147 can exit through the proximal end 114a of the tubular housing 110. Each suture 147 can be any suitable medical grade absorbable or non-absorbable suture.

The anchor pusher 145 is positioned adjacent the suture anchor 137, such that when the anchor pusher 145 is pushed by the suture deploying wire 175, as discussed more fully below, the anchor pusher 145 may, in turn, deploy the corresponding suture anchor 137 from each hollow needle 125. It is to be noted that the anchor pusher 145 may take the shape of the corresponding hollow needle 145 so as to fit and move freely, such as in an inward and outward direction, within each corresponding hollow needle 145.

Figure 6:
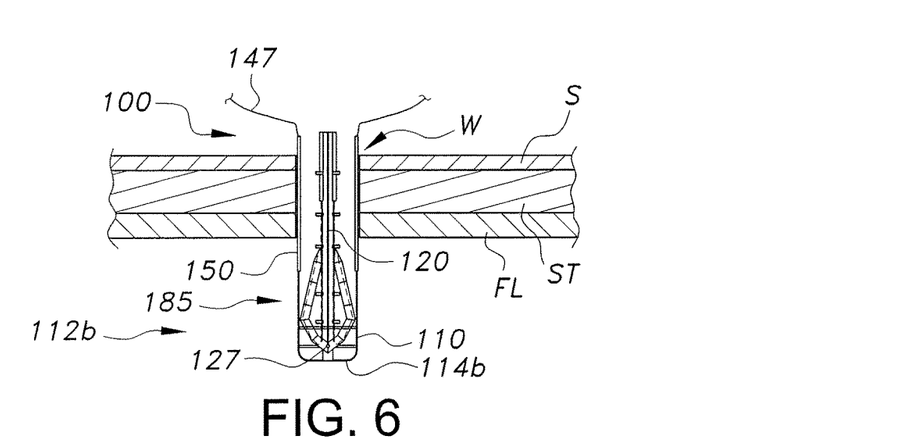
FIG. 6 illustrates the wound closure device penetrating a wound of a patient, according to the present invention.
Figure 7:
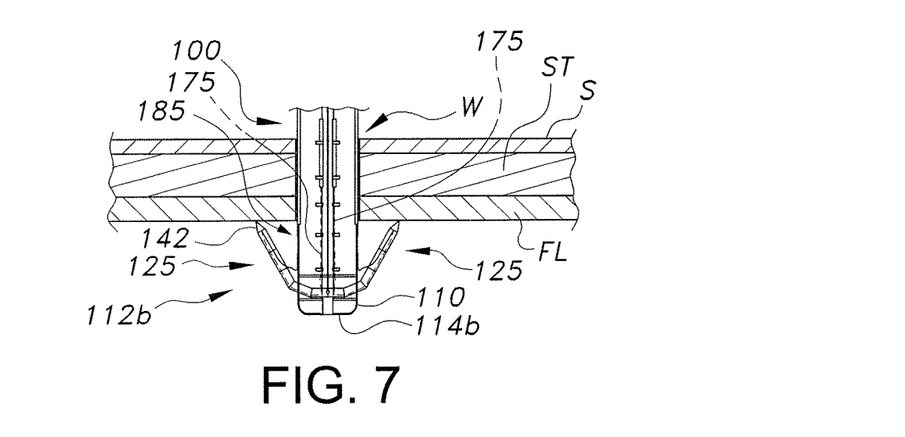
FIG. 7 illustrates each hollow needle extending away from the tubular housing within the wound, according to the present invention.

By way of operation, the medical professional first inserts the distal end 114b of the tubular housing 110 of the device 100 into the wound W to the extent that each needle hatch 185 passes beyond the full thickness of the edge of the wound W, as illustrated in FIG. 6. Once the distal end 114b of the tubular housing 110 is inserted deep enough, the medical professional may rotate the needle control handle 135 in a given direction, such as in a clockwise direction, to deploy and deflect each hollow needle 125 into the wound W. Rotating the needle control handle 135 in the given direction, such as in a clockwise direction, may slide the needle control handle 135 vertically in an upward direction. The upward movement of the needle control handle 135 may, in turn, pull the needle control bar 400 positioned within the track 139 of the needle control handle 135 and the needle control rod 120. By pulling the needle control rod 120 upward, the hinge 127 positioned at the distal end 122b of the needle control rod 120 may be pulled in a corresponding upward direction and, in turn, deflect each of the hollow needles 125 outward through the corresponding needle hatches 185 and away from the tubular housing 110, as illustrated in FIG. 7. It is to be noted that the amount of rotation of the needle control handle 135 of the device 110 may control the degree of deflection (e.g. divergence) of each hollow needle 125 away from the tubular housing 110 within the wound W.

Figure 8:
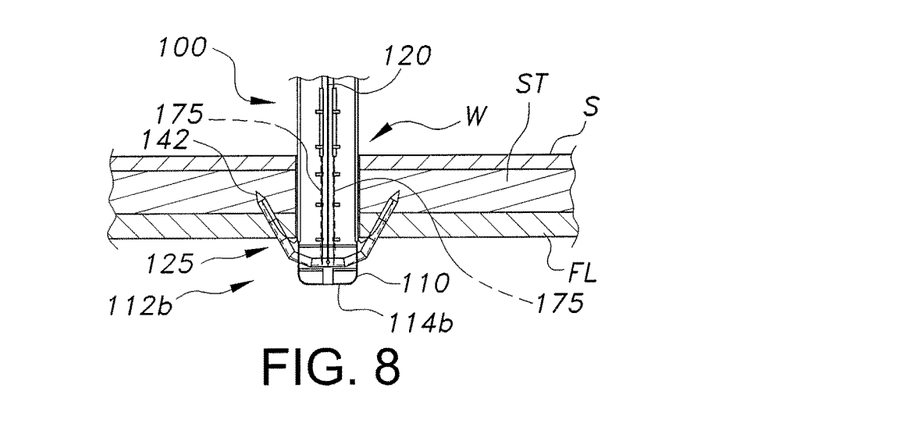
FIG. 8 illustrates each hollow needle attaching to the subcutaneous tissue of the skin surrounding the wound, according to the present invention.
Figure 9:
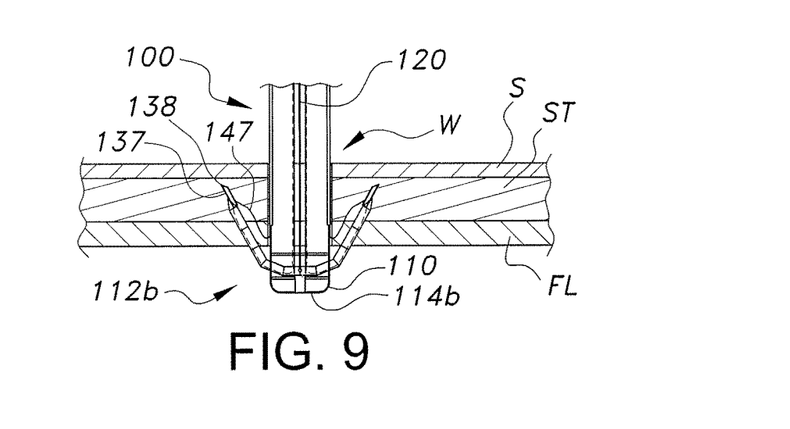
FIG. 9 illustrates the suture anchor being inserted into a layer of tissue surrounding the wound, according to the present invention.

After each hollow needle tip 142 is passed beyond the fascia layer FL in the subcutaneous tissue ST, the medical professional may depress the knob 166 positioned on the proximal end 165a of the suture deploying shaft 164 of the depressible plunger 162 which, in turn, pushes downward on each suture deploying rod 170. The downward pressure exerted on each suture deploying rod 170 pushes each corresponding suture deploying wire 175, which, in turn, pushes the corresponding anchor pusher 145 and deploys each suture anchor 137 beyond the fascia layer FL into the subcutaneous tissue ST surrounding the wound W, as illustrated in FIGS. 8-9. Alternatively, a handle and a trigger mechanism (not shown) can be used in place of the knob 166 to deploy each suture anchor 137 into the fascia layer FL.

Figure 10:
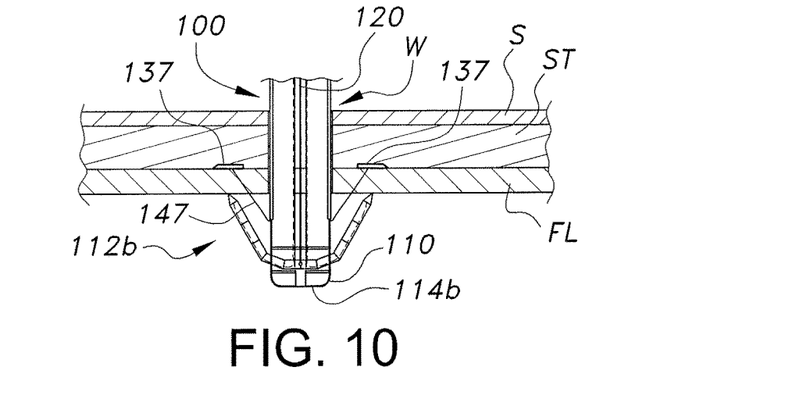
FIG. 10 illustrates each needle detached from the suture anchors, according to the present invention.

When the medical professional has inserted the suture anchors 137 into the fascia layer FL, s/he may release the downward pressure on the knob 166. The counterforce of the compressible member 169 causes the knob 166 to move upward and, in turn, retract each anchor pusher 145 back into its original position, as illustrated in FIG. 10. It is to be noted that the compressible member 169 also limits the downward movement of the suture deploying shaft 164 enough to prevent each anchor pusher 145 from exiting each corresponding hollow needle 125.

Figure 11:
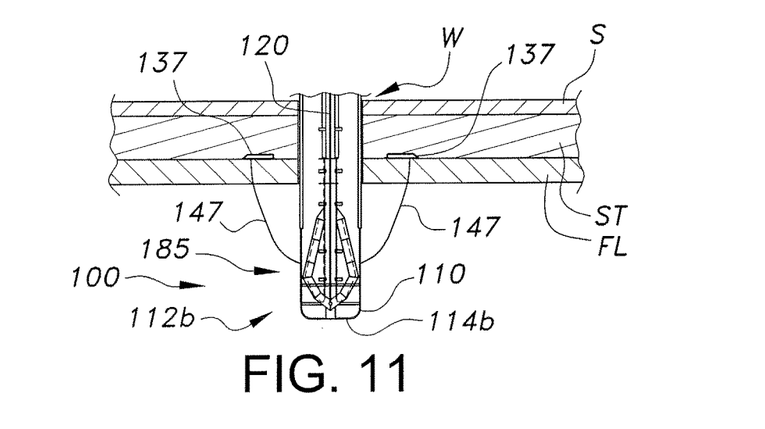
FIG. 11 illustrates the retraction of each hollow needle back into the wound closure device after each suture anchor and corresponding suture has been attached to the layer of tissue surrounding the wound, according to the present invention.

After each suture anchor 137 has been deployed into the fascia layer FL, the medical professional can push the device 100 downward to free each of the hollow needles 125 from the fascia layer FL underlying the wound W, as illustrated in FIG. 10. Once the hollow needles 125 have been freed from the fascia layer FL, the medical professional may rotate the needle control handle 135, such as in a counterclockwise direction, to push the needle control rod 120 and the corresponding hinge mechanism 127 in a downward direction. The downward movement of the needle control rod 120 and the hinge mechanism 127 causes each hollow needle 125 to retract through the corresponding needle hatch 185 back to the original position within the distal portion 112b of the tubular housing 110. The suture anchors 137 and corresponding sutures 147 remain beyond the fascia layer FL surrounding the wound W, as illustrated in FIG. 11.

Figure 12:
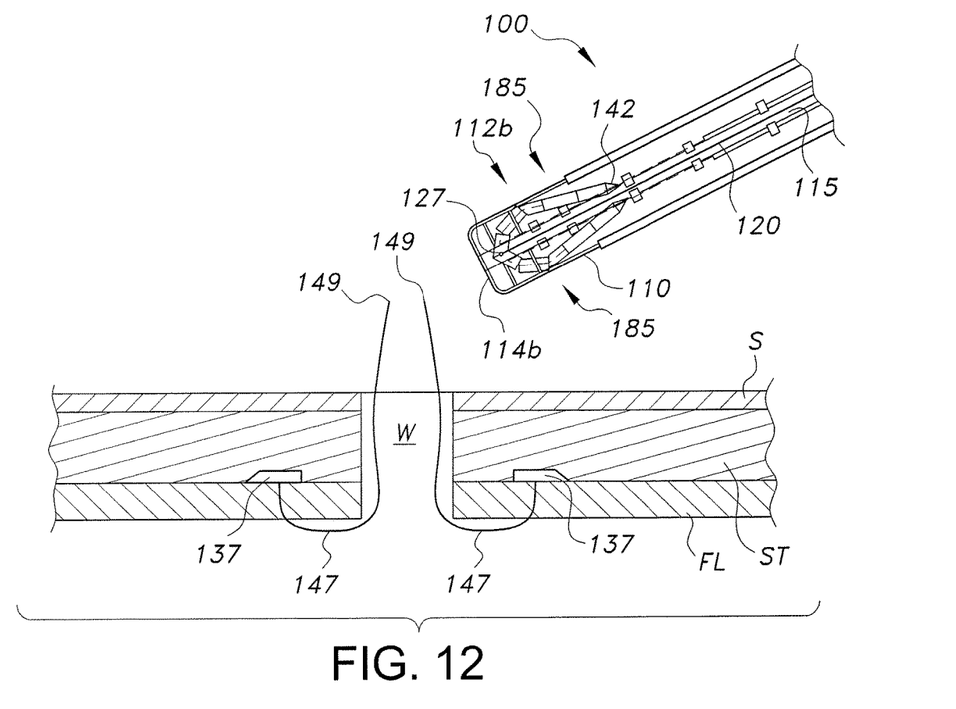
FIG. 12 illustrates the free end of each suture extending out of the wound after the removal of the wound closure device from the wound, according to the present invention.

The medical practitioner may then apply tension to each of the sutures 147 connected to each suture anchor 137. Such tension can cause each suture anchor 137 to flip; thereby, allowing the each suture anchor 137 to become parallel in relation to the fascia layer FL surrounding the wound W to prevent, such as substantially prevent, the sutures 147 from detaching from the fascia layer FL and exiting through the wound W. The device 100 can then be pulled away from within the wound W and the free ends of each suture 147 may be detached from the device 100, as illustrated in FIG. 12. Once the device 100 has been removed and each suture 147 is free, the medical practitioner may tie the free ends 149 of each suture 147 together so as to bring the skin S surrounding the wound W together and close the wound W.

It is to be understood that the present invention is not limited to the embodiments described above, but encompasses any and all embodiments within the scope of the following claims.

I claim:

1. A wound closure device, comprising:
   an outer tubular housing having a proximal portion and a distal portion, the proximal portion of the tubular housing including a pair of opposed side openings, the distal portion of the tubular housing including a plurality of needle hatches;
   an inner shaft disposed within the outer tubular housing, the inner shaft including a pair of opposed side openings in alignment with the side openings of the outer tubular housing;
   a suture deployment assembly including a suture deploying shaft having a diameter greater the inner shaft, a compressible member attached to the suture deploying shaft, a knob at a proximal end of the suture deploying shaft, a plurality of suture deploying rods at a distal end of the suture deploying shaft, a plurality of suture deploying wires attached to the suture deploying rods, a plurality of suture anchor pushers attached to ends of the suture deploying wires;
   a plurality of hollow needles, each hollow needle at least partially housing a respective anchor pusher and a suture anchor;
   a suture having a distal end connected to the suture anchor; and
   a needle control assembly including a needle control rod disposed within the inner shaft, a needle control handle in communication with an outer surface of the tubular housing, a needle control bar connected to a proximal end of the needle control rod and extending through at least a portion of the needle control handle, and a hinge mechanism in communication with a distal end of the needle control rod and pivotally engaged with the plurality of hollow needles,
   whereby rotation of the needle control handle deflects the plurality of hollow needles.

2. The wound closure device according to claim 1, wherein the proximal portion of the tubular housing includes an outer surface having a threaded portion and the needle control handle threadedly engages the threaded portion of the tubular housing.

3. The wound closure device according to claim 1, wherein the tubular housing, the inner shaft, and the suture deploying shaft include side openings, the side openings being in alignment with each other and forming a track, the needle control bar extending through the track.

4. The wound closure device according to claim 1, wherein the suture deploying shaft slidably engages an outer surface of the inner shaft.

5. The wound closure device according to claim 1, further comprising a plurality of stabilizer rings configured for securing each suture deploying rod and corresponding suture deploying wire to the inner shaft.

6. The wound closure device according to claim 1, wherein the compressible member extends between the knob and a proximal end of the tubular housing.

7. The wound closure device according to claim 1, wherein the hollow needle includes a curved portion.

8. The wound closure device according to claim 1, wherein the suture anchor is formed from a biodegradable material selected from the group consisting of polyglycolides, polylacides, polydioxanone, copolymers, and a combination thereof.

* * * * *